United States Patent [19]

Hansen et al.

[11] 4,451,460

[45] May 29, 1984

[54] METHOD AND MEANS FOR REPELLING ANIMALS

[75] Inventors: Helge Hansen; Børje Nyström, both of Stavanger; Eyvin Tørneng, Hinna, all of Norway

[73] Assignee: Nordtend A/S, Stavanger, Norway

[21] Appl. No.: 474,588

[22] PCT Filed: Jul. 2, 1982

[86] PCT No.: PCT/NO82/00039

§ 371 Date: Feb. 23, 1983

§ 102(e) Date: Feb. 23, 1983

[87] PCT Pub. No.: WO83/00417

PCT Pub. Date: Feb. 17, 1983

[30] Foreign Application Priority Data

Jul. 31, 1981 [NO] Norway ............................. 812613

[51] Int. Cl.$^3$ ............................................. A01N 45/00
[52] U.S. Cl. ................................... 424/238; 424/242; 424/243
[58] Field of Search .................. 424/243, 30, 166, 238

[56] References Cited

U.S. PATENT DOCUMENTS 3,694,593 9/1972 Needham et al. ..................... 424/30
4,038,385 7/1977 Bowyer ............................. 424/166

OTHER PUBLICATIONS

Chemical Abstracts, vol. 85, (1976) par. 42,278(g).

Primary Examiner—Elbert L. Roberts
Attorney, Agent, or Firm—Arthur L. Liberman

[57] ABSTRACT

For repelling elk, hart, roe deer and similar animals from plantations, orchards, road sections etc. one or more natural or synthetic steroids of the type occurring on human skin or hair or in human sweat or urine are used. Also derivatives of these steroids obtainable by subjecting the steroids to air, moisture or micro-organisms may be used. The steroids are combined with a carrier into a repellent unit which may liberate molecules of the repellent substance to the air for maintaining a concentration perceptible to the sense of smell of the animals.

9 Claims, No Drawings

METHOD AND MEANS FOR REPELLING ANIMALS

In modern society conflicts may easily arise between different interests with respect to the use of natural resources such as forests, meadows and fields. The parties in this conflict may be numerous, and the individual citizen will often belong to different sides according to the activity exercised at the moment. A rich animal life is for instance very gratifying for those interested in hunting, but constitutes a problem to road users and may cause browsing damages in fields, forest plantations and gardens.

The growth in the number of elk and roe deer has accelerated in the later years, partly because of various game encouraging measures. At the same time the frequency of accidents caused by collision between these animals and cars has become greater and grown into a serious traffic problem (The Highways Department of the Swedish State: The Game Accident Project, May 1980). Even half-wild animals, such as reindeer in the northern part of Scandinavia, cause similar difficulties for the traffic.

Admittedly, browsing damages by elk, roe deer and other wild animals on forest plantations, fields and gardens do not involve personal injuries or death, but has because of the increase in the stock of animals grown to such a size that they are significant both from a private and a social economic viewpoint. It is therefore natural that great efforts are made to find methods for keeping wild and half-wild animals away from the areas which they damage.

The largest effort, at least from a quantitative viewpoint, has been made in connection with game and highway traffic. Acoustic, optical and chemical methods have been used in addition to fences along certain highways. The optical repellent means, primarily game mirrors, have largely proven to be without effect since after a short familiarization period the animals do not mind the mirrors any longer. Also for the acoustic methods tested the familiarization is so fast that the methods are completely without effect in practice.

If fences are made sufficiently high and close, they are effective at least as far as larger animals such as elk and roe deer are concerned. However, cost reasons and the fact that fences hamper outdoor life, indicate that this method for avoiding game accidents cannot be used but to a very limited extent (The Highways Department of the Swedish State: The Game Accident Project, May 1980).

Experiments with smelling repellent means against wild animals have been conducted by numerous parties. Special reference is made to an experiment in which cresol, isobutylalcohol, hartshorn oil, blood meal, thiram and butyric acid have been used as a repellent means against elk. In some cases a certain repellent effect has been observed. However, the experimental design has been such that no definite conclusions about familiarization and other long term effects have been possible (Hans Rosengarten, University of Stockholm, Experiments with Smelling Repellents against Elk, January 1979).

It is known that animals often react to the smell of beasts of prey usually attacking the animal species by running away. Any hunter and outdoor person is familiar with the fact that most wild animals avoid contact with human beings, and that it is the smell which to a great extent makes the animal aware of the presence of human beings. In almost every case, approaching a browsing roe deer in following wind results in a flight reaction, whereas a corresponding attempt in headwind has a possibility of succeeding if normal care is observed. The tendency of the animals to run away when noticing human smell has been utilized by suspending human hair in order to keep fissiped game away from orchards (Cultivation of Fruit and Berries, No. 5, 1979/No. 1, 1980).

It should be observed that the ability of the animals to perceive smells is usually substantially greater than that of human beings. When smell and smell substances are referred to in the preceding and the subsequent paragraphs, the perception of the animals is referred to. The substances referred to as smell substances may sometimes be taken as completely odourless to the less developed sense of smell of human beings. There is reason to believe that the flight reaction of the animals in response to smell of human beings and beasts of prey is instinctive and inherited and to a great extent independent of previous contact with beasts of prey or human beings. If a similar reaction could be used for repellent purposes, advantages such as a reduced risk of familiarization are obtained.

The exact chemical composition of human smell is largely unknown. However, it may be presumed that there are large variations between individuals, and that there are also systematic differences due to age, sex and race. It is known that a large number of various substances may be found in the various secretions from the human body, for instance in sweat and urine. Some of these substances are perceived as odourous by certain persons, whereas others classify them as odourless. However, there are good reasons to believe that there exists a basic structure of smells which characterizes the human being as a species. The compounds in this smell originate from various secretions, primarily from sweat and urine. With respect to sweat the secretions from the so called apocrine sweat glands are of special interest. In human beings these sweat glands are present primarily in the arm pits and in the area around the anal orifice and the genitals. Apart from the direct secretions from the human body also such decomposition products which may formed from these secretions under influence of air, humidity and micro-organisms, especially organisms included in the normal skin flora, probably form part of the smell specific to the species.

Many of the components found in human sweat and urine have also been demonstrated in other mammals. At least some of the substances which may be expected to form part of the smell specific for the species chemically belong to the group of steroids, and many of them have hormonal character. Even the amount of secretion from the apocrine sweat glands is small, and the content of steroids in these secretions constitutes a small fraction of the total amount in the order of 0.02%. This amount is in turn composed of several different steroids, and it may therefore be expected that the amount of individual steroids in secretions from the apocrine sweat glands in human beings is in the order of some picograms or in some cases possibly around one nanogram. Also in the urine the amounts are small, at least if some specific pregnancy hormones in pregnant women are excepted. The occurrence of steroids in secretions from the apocrine sweat glands, which must probably be regarded as the "smell glands" of humans similar to the corresponding glands in other mammals, makes it probable that steroids constitute a not insignificant part of the smell specific for the species. Differences between various mammals with respect to the smell should then be referred to the amount and balance between the various components.

In human sweat and urine the following steroids have been determined:
androst-4-en-3,17-dione,
androsterone,
dehydroepiandrosterone,
preg-5-en-3β-ol-20-one,
5α-androst-16-en-3α-ol,
5α-androst-16-en-3-one,
testosterone,
11-keto-aetiocholanalone (3α-hydroxy-5β-androstan-11,17-dione),
i-androstanalone,
oestrone,
oestriol,
oestradiol,
androstan-3-one,
16-androstene-3-ol,
progesterone and
pregnandiol.
As oxidation products
androstadien-17-one and
androst-2-en-17-one
have been reported.

With a view to the complicated composition of the secretions from human smell glands, i.e. the apocrine sweat glands, it is surprising that individual components and combinations of a few components of the secretions have proved to exhibit repellent effects on animals comparable to or exceeding the effect of human smell from for instance suspended used working cloths and human hair. The substances, the repellent effect of which in this respect has been studied in detail, all chemically belong to the group of steroids and are synthetic or semi-synthetic substances corresponding to the steroids which have been demonstrated in human skin and hair, including body hair, or in human sweat or urine.

Means containing steroids which may be of a hormonal character have been widely used both in medicine and in domestic animal care.

Individual steroids and compositions containing two or more steroids are certainly well applicable to obtain a repellent effect on wild animals. However, the sometimes high biological activity of the steroids constitutes a handling problem. The high costs of producing steroids also indicate that an attempt must be made to obtain an optimal utilization by controlling the liberation to the atmosphere in a suitable manner. The problems involved in the handling of the steroids and in the control of the liberation to the atmosphere are best solved by combining the steroids or the steroid composition with a carrier into a repellent unit.

The choice of carrier and the design of the repellent unit may be effected in many different ways which are adapted to various conditions of use. However, an essential condition is that the repellent unit, i.e. the combination of the steroid preparation and the carrier, can liberate steroid molecules to the air at a controlled rate so that a sufficiently high and uniform concentration can be maintained in the air surrounding the repellent unit in a desired period.

The present invention relates to a method for repelling animals, characterized by the use as a repellent substance of one or more steroids which are synthetic or have been extracted from naturally occurring materials, and which are of the type occurring on human skin or hair or in human sweat or urine and/or one or more of the derivatives thereof obtainable by subjecting the steroids to air, moisture or micro-organisms, in such a manner as to provide in the air a concentration perceptible to the sense of smell of the animals.

The invention also provides a means of repelling animals, characterized in that as a repellent substance it contains one or more steroids which are synthetic or have been extracted from naturally occurring materials, and which are of the type occurring on human skin or hair or in human sweat or urine and/or one or more of the derivatives thereof obtainable by subjecting the steroids to air, moisture or micro-organisms, and that this repellent substance is combined with a carrier into a repellent unit capable of liberating molecules of the repellent substance into the air for maintaining a concentration perceptible to the sense of smell of the animals.

It is possible to extract the said steroids and their derivatives from human sweat and urine, but for obvious reasons only synthetic products are used in practice. Raw materials for the synthesis may for instance be steroid-alkaloids which may be recovered from certain plant parts or cholesterol. Also fully synthetic methods using petroleum products as starting materials are possible. The methods of the synthesis may be purely chemical, biochemical or microbiological or various combinations of these methods. In some cases it may be advantageous to use an intermediate product from the synthesis, deleting for instance the final separation or purification step.

As indicated the naturally occurring amounts of steroids in human secretions are very small. Considering that relatively large molecules are involved, their vapour pressure must be presumed to be very low. However, it is known that the sense of smell of animals and human beings is often so sensitive that no measuring instrument comes up to it. The experiments carried out have not made it possible to establish any lower limit for the amount below which no effect of the said steroids may be observed. However, it can be assumed that any such limit lies below the level corresponding to the presence of the steroids in human secretions. For reasons of handling and because of the wish to maintain a sufficiently high concentration in the atmosphere in a not too short period, the amounts used cannot be too small. A practical lower limit should be about 1 ng of steroid for each repellent unit.

It is in the nature of the case that the amount used for each repellent unit should be kept as small as possible, not at least for cost reasons. However, as far as it has been possible to ascertain there are nothing indicating that large amounts should have negative effects from a technical point of view. It is therefore not possible to state any upper limit since it would be completely dependent upon how the means is to be applied and how long it is desired to maintain the repellent effect. In preferred embodiments of the invention the steroid amounts have varied between 0.1 μg and 100 mg, preferably between 1 μg and 100 mg for each repellent unit.

The steroids occurring on human skin and hair and in human sweat and urine can at least in part have hormonal properties. When carrying out the present invention a hormonal effect is an undesired side effect. For this reason it is preferred to use steroids having as small a hormonal effect as possible.

In practical experiments various steroids including the following have been used: testosterone, androsterone, dehydroepiandrosterone, 11-ketoaetiocholanalone, i-androstanalone, oestrone and androstenol. These steroids are the quantitatively most significant in secretions from apocrine sweat glands in male human beings.

Dehydroepiandrosterone and androsterone combine a relatively low hormonal effect with a very good repellent effect. They may advantageously be used either separately or in combination with each other and/or with other steroids. Combinations of two or more steroids are often preferable, since they supplement the repellent effect of each other and provide a repellent smell which is closer to the smell of human beings. In this manner a synergetic effect may be obtained which above all is reflected in a reduced tendency of familiarization. The content of the individual steroids may also be kept lower, which reduces the risk of specific hormonal effects in the production and handling.

As already mentioned it is advantageous to combine the said steroids with a suitable carrier when carrying out the invention in practice. One purpose of the carrier is to protect the steroid preparation against loss by mechanical contact. The carrier should further protect the steroids against moisture which may release active substance and lead to inactivation of the repellent effect. However, the most important effect of the carrier is, together with the steroid preparation, to form a combination which liberates steroid molecules to the air at a rate which is controllable to as large an extent as possible.

The combination of carrier and steroid composition is in practical use subjected to very different conditions with respect to temperature, air flow etc. An increase of the temperature raises the vapour pressure of the steroids, whereas an increase of the air velocity enhances the liberation of active material by reducing the degree of saturation over the preparation. Both effects result in faster consumption of the repellent substance. Whereas an increased liberation of steroid molecules to the atmosphere may be desirable and necessary at increasing wind velocity in order to compensate for the dilution caused by the higher wind velocity, the increase at higher temperatures is presumably not desirable. It may be convenient to modify the vapour pressure of the steroid composition, for instance by dilution with some form of solvent which may be present in solid or liquid form. By a suitable choice of diluent it is also possible to see to it that the liberation at low temperatures is not reduced to unacceptably low values.

Other possibilities of control with the rate of liberation involves controlling the liberation to a larger or lesser extent by diffusion, for instance by making the carrier of a microporous material or by encasing the steroid preparation in a membrane having a limited permeability. Other embodiments in which the diffusion may provide a substantial part of the control mechanism for liberation of repellent substance involve letting the steroid composition and the carrier forming a gel which may be shrinking or not shrinking depending on whether or not also other components are liberated to the atmosphere together with the steroid molecules.

A further possibility for controlling the liberation rate is to use carrier materials having the capacity of absorbing the repellent substance and having a large surface area for each unit of volume, for instance activated charcoal or colloidal or pyrogenic silica. A large number of different methods for controlling the liberation of active substances to the environment are known, and it does not cause substantial difficulties for a man skilled in the art to combine various methods in a convenient manner in order to achieve the desired result.

With respect to the choice of material for the carrier there are in principle no restrictions. As an example porous ceramic bodies, native or regenerated cellulose, natural or synthetic polymers of various types in filament form or as microporous or macroporous moulds or as gel forming substances may be used. There may further be used inorganic materials having a large specific area, for instance certain silica compounds such as zeolites, fine-grained clays etc. In many cases it is advantageous to use several different materials in combination to obtain the desired result. The technique in this respect is well known to those skilled in the art.

Whereas the steroid preparation and the carrier should be combined in protected environments, for instance in a laboratory or in a manufacturing plant, the final shaping may take place either in direct connection with the combination of the steroid preparation and the carrier or locally when applying it to the final place of application.

In the former case a moulded body is produced which may have any desired shape, for instance tape, strip, sheet, plate, rod, tapering or spherical form. This moulded body is advantageously provided with some casing protecting against precipitation and preventing direct contact with the steroid containing body, while still allowing passage of steroid molecules in vapour form. Further, the casing should be provided with some form of suspension or fastening device or be designed so as in itself to provide a fastening device in order to permit a stable positioning in the place of application. Suitable embodiments include tapes or strips which are wound around tree trunks, posts etc. and fastened by adhesion, nailing or tieing.

In the second case the carrier and the steroid preparation are suitably combined to a viscous liquid or paste, which in the place of application is applied directly to solid objects such as posts, tree trunks, mountain shelves etc. The liquid may be applied by being displaced from a container by means of a propulsion gas or by pumping. Another possibility is to effect the application from a tube or a collapsible plastic bottle. In order to avoid that the persons involved in the application are subjected to unnecessary inhalation of the steroids, it is convenient to avoid such spray methods in which the material leaves the container as an aerosol, whereas pressure containers or pumps dispensing the material as a foam or a gel string can advantageously be used.

When the material is dispensed in the form of a foam the latter may be of the disintegrating type or of the type forming a permanent macroporous foam structure. In the local application in a manner as described above, it is often advantageous when the combination of the carrier and the steroid preparation also contains substances which provide a good adherence to the stationary surfaces on which the application takes place. Further, the initially liquid or pasty material should relatively quickly be transformed into a body which is solid at least on the surface and which only with substantial difficulty can be removed from the substrate. By the term "body" in this context also relatively thin films such as lacquer coatings are referred to. It is of course possible to apply the combination of the steroid preparation and the carrier by coating with a brush or a filler knife etc., but this is a less preferred method considering that personnel then has less opportunity of avoiding direct skin contract with the steroid preparation.

In the case of local application the term repellent unit may be less unambiguous. However, it is in the nature of the case that the application should take place spot-wise or dot-wise, and the term repellent unit will then relate to each separate application surface.

If the area to be protected against intrusion by wild animals is very small, for instance a small number of fruit trees in a garden in a residential district, it may be sufficient with only one or a few repellent units. In most cases, however, larger areas are involved, such as forest plantations, large orchards and not at least highways trafficked by motor vehicles. In these cases a relatively large number of repellent units must be placed along the border of the area in question. The largest possible distance between the repellent units is then determined by the strength of the preparations, and a balance must be found between the wish to have as few units as possible and the amount of steroids which without hesitation may be placed in a repellent unit. Other factors which also influence the choice of the distance between the units and the necessary amount of repellent substance in each unit are expected normal wind velocities, temperature conditions, requirements for high security against tampering, the required time of protection or the period between replacement etc. The distance between the units may in extreme cases be chosen less than 1 m or more than 100 m. In ordinary cases the most suitable distance is believed to be between 5 and 50 m. Usually 10 to 30 m is a suitable distance between the units. When the substance is applied locally, the shortest of the distances referred to above is often preferable since it does not substantially increase the effort if more units are placed.

At low and medium wind velocities the flow of air is laminar and parallel to the ground. The liberated steroid molecules substantially follow the flow of air and move relatively slowly in vertical direction. For an optimal utilization of the repellent substance it is therefore convenient to position the repellent units at a level above the ground which is adapted to the animal species to be influenced. A too high positioning may result in the wind sweeping the steroid molecules away so that they cannot come into contact with the olfactory organs of the animals. A too low positioning causes the molecules too soon to come into contact with the ground surface where they are bonded and inactivated. For elk and roe deer the most convenient positioning in the vertical direction is between 0.5 and 2.0 m above the ground. It is also within this area that the smell glands of an upright person will be found.

Below a number of examples of the use of steroids and repellent units for keeping roe deer away from gardens and elk and roe deer away from highways are given. The choice of the animal species and the experimental area are determined entirely by experimental considerations and must not be regarded as limiting, since those skilled in biology will be perfectly aware of the fact that similar effects may be expected in other areas and with other groups of animals avoiding contact with human beings and using the sense of smell when adapting to the surroundings. Similarly, it is a matter of course for those skilled in chemistry that other carriers for the steroid preparations will give analogical results, provided that the design has been chosen so as to satisfy the previously mentioned requirements of a continuous liberation of steroid molecules to the atmosphere.

EXAMPLE 1

Extraction sleeves (30×80 mm) were impregnated with androsterone by an addition of 1 ml of a 1% solution of androsterone.

The repellent units (extraction sleeves) were suspended at intervals of 10 m around an orchard, in which browsing damages caused by royal stag had regularly occurred. In an experimental period of 4 days no visits of royal stag occurred. The repellent units were then removed and the orchard watched for browsing damages for 4 days. Already the first night the orchard was visited by royal stag which caused browsing damages. These visits were repeated for the subsequent days.

Another experiment, this time with extraction sleeves impregnated with 10 mg dehydroepiandrosterone, was carried out. Again, no sign of royal stag or browsing damages could be observed during a period of 4 days. During a new control period without the suspended repellent units, the stags returned to the orchard already the first night and caused browsing damages. The browsing continued for the subsequent nights.

The experiments were conducted in the month of February.

EXAMPLE 2

In this case a nursery with large plantations of fruit trees was used for the field experiment. The plantations had frequent visits of both royal stag and roe deer causing substantial browsing damages.

The experiments were conducted in the period February to April. Most of the time the ground was covered by snow so that it was easy to record visits of stag and roe deer in the plantations and their surroundings.

Repellent units of the same type as described in Example 1 were prepared, this time impregnated with 10 mg androsterone and 10 mg dehydroepiandrosterone in combination. The repellent units were suspended at intervals of 10 m around the field. The sleeves were covered by plastic film to protect them against precipitation.

During the first 7 days there were no records of roe deer or stag in the protected area. The 7th night one roe deer entered the area. The tracks showed that the animal had been restless, and that it had soon disappeared without browsing on the fruit trees.

After this observation there was no recorded visit from roe deer or stag during 38 days.

On the 45th day counted from the beginning of the experiments tracks were recorded of a stag which had acted similarly to the roe deer previously referred to. Neither this animal had browsed on the fruit trees.

The tracks of a herd of 12 to 15 stags and several roe deer regularly appeared in the vicinity of the experimental area during the experimental period, but traces of these animals were not found closer than approximately 100 m from the protected area, except for the two cases referred to above.

After 45 days the repellent units were removed. Already the first night the plantations were visited by both roe deer and royal stag which caused substantial browsing damages.

EXAMPLE 3

This experiment was conducted in a geographically isolated area having a numerous stock of roe deer. In this area there was an orchard which was the object of browsing damages from roe deer. Because of the geographical isolation and the density of roe deer there was reason to believe that the normal caution of the animals and the fear of human beings may have been reduced.

Repellent units of the same type as described in Example 2 were suspended in the outskirts of the orchard at intervals of about 10 m.

The ground within and immediately around the orchard consisted of loose soil which made it easy to record the movements of the animals in the area.

Before the start of the experimental period visits and browsing damages by 3 to 5 animals each night were recorded. After the repellent units were positioned no visit of roe deer was recorded for an experimental period of 45 days.

On two occasions during the experimental period tracks of roe deer were recorded in the vicinity of the orchard. In those instances the animals had approached the protected area in following wind and in high speed, and halted about 25 m from the repellent units and returned in long leaps.

When the repellent units were removed at the end of the experimental period the roe deer returned already the first night in the same amount as previously with resulting substantial browsing damages.

EXAMPLE 4

This experimental series was conducted in a forest area having a dense population of elk and roe deer. An approximately 600 m long section of gravelled forest road was chosen as an experimental area. By regular inspection it was possible to register how many animals followed or crossed the road, since it was possible to read the tracks even in dry periods.

In a control period of 6 days before the first repellent experiment there were on the average 5 passages of elk and 2 passages of roe deer each day.

Extraction sleeves impregnated with 10 mg androsterone for each sleeve were suspended on both sides of the road at intervals of about 20 m. During an experimental period of 10 days no elks or roe deer passed the protected section of the road. By inspecting other sections of the forest road it was possible to establish that there were still animals in the area.

During a control period of 4 days after the repellent units had been removed there were on the average 4 passages of elk and 1 passage of roe deer each day.

Corresponding experiments were carried out on the same road section with repellent units impregnated with 10 mg dehydroepiandrosterone, i-androsterone, oestrone, androsterone and 11-ketoaetiocholanalon, respectively. In all experiments the repellent units were suspended for 10 days, whereas the control period was 4 days as in the first experiment. During the control periods between 3 and 7 passages of elk and between 1 and 3 passages of roe deer each day were observed. During the experimental periods an average of 1 passage of elk each day was never exceeded. In no instance the animals had followed the entire road section, which was frequently the case during the control periods.

EXAMPLE 5

This experiment was conducted in an area having a dense elk population, and as in Example 4 a gravelled forest road was used. The length of the experimental period was 10 days as in Example 4, the control period being 4 days.

Repellent units prepared from extraction sleeves as in Examples 1 to 4 were used. The sleeves were impregnated with the following steroid combinations:

(a) 10 mg androsterone and 10 mg dehydroepiandrosterone.
(b) 1 mg androsterone and 20 mg testosterone.
(c) 100 mg dehydro-epi-androsterone and 5 mg 11-ketoaetiocholanalone.
(d) 0.1 mg androsterone and 60 mg androstanalone.
(e) 25 mg androsterone and 25 mg androstenol.
(f) 30 mg testosterone, 10 mg dehydroepiandrosterone and 0.05 mg oestrone.

In the experimental periods with the combinations a and c there were no passages of elk, whereas up to one passage of elk each day was observed with the remaining steroid combinations.

In the control periods between the experiments between 4 and 7 passages of elk each day occurred.

EXAMPLE 6

In these experiments the repellent units were manufactured from conical aluminum sleeves having an inner coating of cellulose. The cellulose coating was impregnated with acetone solutions of various steroid mixtures as indicated below.

An orchard situated in a district having a very dense population of roe deer and being pested by roe deer browsing on the fruit trees, was used an experimental area.

Before the experimental series was started an average number of 6 roe deer each night visiting and browsing in the orchard was recorded by observation of track prints in the soft ground. The repellent units were suspended at intervals of 7 m around the orchard and approximately 1.5 m above the ground. Observations of track prints were made each morning. Each evening the ground surface was raked to facilitate observation of any track prints.

| Experiment | Steroid mixture | mg in each unit | Experimental period, days | Total number of roe deer in the period |
|---|---|---|---|---|
| g | cortisone | 10 | 8 | 1 |
|   | progesterone | 10 |   |   |
| h | none |   | 4 | 18 |
| i | corticosterone | 5 |   |   |
|   | androsterone | 5 | 8 | 0 |
|   | 11$^d$-desoxy-cortisol | 5 |   |   |
| j | none |   | 4 | 21 |
| k | corticosterone | 5 | 8 | 0 |
|   | 11$^d$-desoxy-cortisol | 5 |   |   |
|   | cortisone | 5 |   |   |
|   | progesterone |   |   | 2 |
| l | none |   | 4 | 16 |
| m | androstenol | 1 |   |   |
|   | cortisone | 10 | 8 | 3 |
|   | corticosterone | 10 |   |   |
| n | none |   | 4 | 19 |
| o | prednisolone | 10 |   |   |
|   | oestriol | 3 | 8 | 1 |
|   | 21-desoxy-cortisone | 5 |   |   |

EXAMPLE 7

This experiment was conducted in order to study the long term effect of the repellent substance. An orchard situated on an island surrounded by open water the year round was chosen as an experimental area. A large population of roe deer and a smaller population of hart were present on the island. The total damage on fruit trees and other useful plants by the animals was very extensive. Because of the isolated situation of the island it may be presumed that no or at most sporadic communication with other populations of deer and hart occurs.

The repellent units were shaped in the same manner as described in Example 6, i.e. they consisted of conical aluminium sleeves having an inner coating of cellulose. The cellulose coating was impregnated with an acetone solution of steroids in such an amount that each repellent unit contained 10 mg dehydro-epi-androsterone and 10 mg androsterone.

The repellent units were suspended around the orchard at intervals of about 8 m and approximately 1.5 m above the ground. Except for shorter control periods the experiment lasted for 18 months, which involved that a new generation of animals experienced the repellent substance, and that it should be possible to observe any familiarization effects.

The experimental area was inspected every day for trace of deer and hart. Depending on the time of the year it was possible to observe traces either as track prints in snow or loose soil or as fresh browsing damages on trees. Four control periods of one week each were included in the experimental period. During the control periods all the repellent units were removed. During all the four control periods numerous visits of deer and hart could be observed already the first night.

During the experimental periods, in which the repellent units were suspended, no visits of deer and hart were observed with the following exceptions:

Days 48 to 50: Visits of 2 to 3 animals each night. During this period there was heavy wind with a wind force of between 15 and 25 m/s, and some of the repellent units were destroyed. After the weather had improved and the damaged units replaced the protection was again effective.

Day 63: One animal entered, but the track prints showed that the animal had quickly turned around and returned the way it entered.

Days 92 to 96: Traces of one animal were found each morning. A closer inspection disclosed that the animal concerned was a lonely one year old roe fawn which seemed to be hurt. The animal was killed and an examination of the body showed that one of the legs was heavily damaged by shot.

Days 207 to 212: Visits by several animals each night. During this period there was heavy wind and snow fall, and the number of animals was consequently difficult to ascertain.

Days 369 to 370: Visits by one and two animals respectively. External reasons why the animals had entered could not be determined.

Day 486: One animal had entered and according to the track prints it had run back and forth, whereupon it had left the area in long leaps.

During the entire experimental period animals and traces of animals could be observed in the vicinity of the experimental area. Traces could be observed as close as 25 m from the suspended repellent units.

The term steroids may seem comprehensive, but this is not true regard being had to the fact that steroids form a very well defined group of chemical compounds having a common basic structure and varying only slightly as far as substituents and double bonds are concerned. The steroids used in the experiments have been carefully selected in order to form a representive selection of the group of substances defined in the claims.

As appearent from the claims the invention is restricted to the use of individual or a small number of steroids at a time. The steroids used are synthetic or extracted from naturally occurring materials by any suitable chemical or physical isolation process.

We claim:

1. A method for repelling animals by placing smelling repellent substances in the area from which the animals are to be kept off, characterized by the use as a repellent substances of one or more steroids which are synthetic or have been extracted from naturally occurring materials and which are of the type occurring on human skin or hair or in human sweat or urine and/or of one or more of the derivatives thereof obtainable by subjecting the steroids to air, moisture or micro-organisms in such a manner as to provide in the air a concentration perceptible to the sense of smell of the animals, said steroids being selected from the group consisting of testosterone, androsterone, dehydroepiandrosterone, 11-ketoaetiocholanalone, i-androstanalone, oestrone and androstenol.

2. The process of claim 1 further characterized by the use as a repellent substance of androsterone or dehydroepiandrosteone or mixtures comprising androsterone and dehydroepiandrosterone.

3. Means for repelling animals, characterized in that as a repellent substance it contains one or more steroids which are synthetic or have been extracted from naturally occurring materials, and which are of the type occurring on human skin or hair or in human sweat or urine, and/or of one or more of the derivatives thereof obtainable by subjecting the steroids to air, moisture or micro-organisms, and that this repellent substance is combined with a carrier into a repellent unit capable of liberating molecules of the repellent substance into the air for maintaining a concentration perceptible to the sense of smell of the animals, further characterized in that said steriods are selected from the group consisting of testosterone, androsterone, dehydroepiandrosterone, 11-ketoaetiocholanalone, i-androstanalone, oestrone and androstenol.

4. The process of claim 3 further characterized in that the steroid is androsterone or dehydroepiandrosterone or mixtures comprising androsterone and dehydroepiandrosterone.

5. The process of claim 1 further characterized in that the repellent substance is a mixture of two or more steroids or steroid derivatives and the steroids are selected from the group consisting of testosterone, androsterone, dehydroepiandrosterone, 11-ketoaetiocholanalone, i-androstanalone, oestrone and androstenol.

6. Method according to claim 1 characterized by placing one or more repellent units on or at the borders of the area from which it is desired to repel the animals.

7. The process of claim 1 characterized by placing one or more repellent units on or at the borders of the area from which it is desired to repel the animals and further characterized in that the amount of repellent substance for each repellent unit is between 1 ng and 100 mg.

8. Means according to claim 3 characterized by the amount of repellent substance in each repellent unit being between 1 ng and 100 mg.

9. Means according to claim 8 characterized in that the repellent substance is androsterone or dehydroepiandrosterone or mixtures consisting of androsterone and dehydroepiandrosterone.

* * * * *

UNITED STATES PATENT AND TRADEMARK OFFICE
CERTIFICATE OF CORRECTION

PATENT NO. : 4,451,460
DATED : May 29, 1984
INVENTOR(S) : Helge Hansen, Borje Nystrom, Eyvin Torneng It is certified that error appears in the above-identified patent and that said Letters Patent are hereby corrected as shown below:

Column 10, line 55, in the Table at column 3, add the number:

---2---

Column 10, line 52, column 2 should read:

---11α-desoxy---

Column 10, line 49 of the Table at column 2, should read:

---11α-desoxy---

Signed and Sealed this

Thirteenth Day of November 1984

[SEAL]

Attest:

GERALD J. MOSSINGHOFF

Attesting Officer

Commissioner of Patents and Trademarks